US 6,949,220 B2
(12) United States Patent  
Abe

(10) Patent No.: US 6,949,220 B2  
(45) Date of Patent: Sep. 27, 2005

(54) ARTIFICIAL HEART-LUNG APPARATUS

(75) Inventor: Yusuke Abe, Tokyo (JP)

(73) Assignees: Isao Nemoto, Chiba-Ken (JP);  
Shigemasa Osaki, Sandy, UT (US)

( * ) Notice: Subject to any disclaimer, the term of this patent is extended or adjusted under 35 U.S.C. 154(b) by 0 days.

(21) Appl. No.: 10/702,906

(22) Filed: Nov. 5, 2003

(65) Prior Publication Data

US 2004/0097861 A1 May 20, 2004

(30) Foreign Application Priority Data

Nov. 7, 2002 (JP) ........................................ 2002-324244

(51) Int. Cl.[7] ............................. A61M 1/14; A61M 1/36
(52) U.S. Cl. ........................ 422/45; 422/48; 604/6.11; 604/6.14; 261/DIG. 28
(58) Field of Search ................ 422/44–48; 604/4.01, 604/6.11, 6.13–6.14, 93.01, 27, 30, 113, 131, 151–5; 261/1, 158–9, 19–21, 24, 28–9, 75, 83–85, DIG. 28; 600/16–18; 415/900; 165/58, 60; 417/65–7, 85–6

(56) References Cited

U.S. PATENT DOCUMENTS

| | | | |
|---|---|---|---|
| 4,610,656 A | | 9/1986 | Mortensen |
| 5,044,882 A | * | 9/1991 | Akamatsu ................. 415/182.1 |
| 5,308,314 A | | 5/1994 | Fukui et al. |
| 5,352,103 A | | 10/1994 | Auer |
| 5,411,378 A | * | 5/1995 | Sipin ........................... 417/360 |
| 5,499,907 A | | 3/1996 | Knott et al. |
| 5,728,069 A | * | 3/1998 | Montevecchi et al. ....... 604/151 |
| 6,387,323 B1 | * | 5/2002 | Afzal et al. .................... 422/45 |
| 6,428,747 B1 | * | 8/2002 | Dueri et al. ................... 422/46 |
| 6,547,753 B1 | | 4/2003 | Plunkett et al. |
| 6,572,821 B2 | | 6/2003 | Knott |
| 2002/0031442 A1 | | 3/2002 | Knott |

FOREIGN PATENT DOCUMENTS

| | | |
|---|---|---|
| EP | 0 705 610 A1 | 4/1996 |
| JP | 06-002668 | 11/1994 |
| JP | 2000-093509 | 4/2000 |

OTHER PUBLICATIONS

Yusuke Abe, et al., "Principle of the Rotary Undulation Pump", *Journal of Artificial Organs*, Jun. 2002, pp. 84–90, vol. 5, No. 1.

Jürgen Hahn, et al., Determining Flow and Pressure in a Bearingless Pump from the Position Signals and Motor Currents, *International Power Electronics Conference*, Apr. 307, 2000.

Itsuro Saito, et al., "Progress in the Control System of the Undulation Pump Total Artificial Heart", *Artificial Organs*, Jun. 2003, pp. 27–33, vol. 27, No. 1.

* cited by examiner

*Primary Examiner*—Patricia Bianco  
(74) *Attorney, Agent, or Firm*—Stephen A. Slusher; Peacock Myers & Adams, PC

(57) ABSTRACT

An integrated, artificial heart-lung machine and method for performing extracorporeal blood oxygenation and circulation. The heart-lung machine is a single unit in which a cylindrical artificial lung, preferably with a heat exchanger, is connected in series to an undulation pump and a removable drive unit. The undulation pump is directly connected to the oxygenator which significantly reduces the blood priming volume of the system.

19 Claims, 11 Drawing Sheets

ARTIFICIAL HEART-LUNG APPARATUS

BACKGROUND OF THE INVENTION

1. Field of the Invention (Technical Field)

The present invention relates to an artificial heart-lung apparatus including an artificial lung or oxygenator, and a pump, and more particularly an undulation pump with a precessional movement.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

An artificial heart-lung machine is often necessary for performing heart surgery, especially open-heart surgery. A conventional heart-lung machine includes a pump that transports the blood of a patient in an extracorporeal circuit through flexible tubing to an artificial lung unit for oxygenation of the blood and a heat exchanger unit for maintaining the blood at a predetermined temperature. One of the goals in designing a heart-lung machine is to minimize the circuit priming volume. A low priming volume is advantageous for minimizing dilution of the patient's blood, which often aids in patient recovery. Furthermore, a low priming volume may decrease the amount of transfusion required and may reduce the amount of medication that is needed following surgery.

Much medical research has been devoted to minimizing the priming volume of heart-lung machines. However, heart-lung machines currently in use or under development consist of a large artificial lung and pumping system which are located outside the vicinity of the patient's surgical area and must be operated by a perfusionist. At present heart-lung machines are connected to a patient by long tubes that transport blood between the patient and the machine. The size of the machine and the distance from the patient are obstacles to reducing the priming volume of heart-lung machines. Another problem with heart-lung machines is that they are large and occupy an inefficient amount of space in operating rooms.

One potential solution is to construct a smaller heart-lung machine equipped with a small centrifugal pump that can be used in proximity to the surgical area. However, centrifugal pumps have a cone shape with a drive unit at the bottom, an inlet port that opens in the direction of the axis, and an outlet port that opens in the direction of the circle. The shape of the centrifugal pump makes it impossible to construct an integrated unit in which the pump, drive and lung units are directly connected in series, and thus makes it difficult to design a heart-lung machine which is small enough to be used near the patient's surgical area.

There is thus a need for a heart-lung machine that is both robust and compact, such that it can be positioned immediately adjacent the patient. There is further a need for a heart-lung machine in which the pump, drive and lung units are directly connected in series, thereby minimizing the size of the machine.

BRIEF SUMMARY OF THE INVENTION

The invention provides an integrated heart-lung machine that includes an undulation pump, an oxygenator, a heat exchanger, and a removable drive unit that is attached to the undulation pump. In a preferred embodiment the undulation pump, oxygenator, and heat exchanger are interconnected in series.

The invention further provides an artificial heart-lung machine that includes a cylindrical oxygenator with hollow fiber membranes for blood gas exchange and a cylindrical undulation pump, coaxial with the oxygenator, to pump blood to the oxygenator. In a preferred embodiment the oxygenator, the undulation pump, and a drive unit for driving the pump are all coaxial. The drive unit may further be removable from the undulation pump, and the heat exchanger may be located inside of the oxygenator. The heat exchanger has a first channel plate that forms a blood channel and a second channel plate that forms a media channel for heating or cooling of blood. In a further embodiment the heat exchanger has a plurality of first channel plates that provide blood running channels and a plurality of second channel plates that provide media running channels, disposed such that the first and second channel plates are adjacent to and alternating with each other.

In yet another embodiment, the invention provides an artificial heart-lung apparatus with a cylindrical blood pump with an outlet at one end that is directly connectable to an inlet port of an oxygenator, further optionally with a drive unit that is removable from the blood pump. A cylindrical oxygenator may be directly connected to the blood pump, and the drive unit is connected to the pump on the side opposite from the oxygenator. In one embodiment the blood pump has a toroidal-shaped pump chamber with a circumferential flexible liquid-tight inner wall, two substantially angled side walls, an arc-shaped outer wall, an inlet port and an outlet port. A circular undulation paddle transits the flexible liquid-tight inner wall and has a diameter that extends to the arc-shaped outer wall of the pump chamber with a paddle coupler that is centrally disposed on the undulation paddle and receives a precessional motion. The drive unit has a motor rotor, a free rotating drive shaft angled with respect to the axis of the motor rotor, and a drive shaft coupler at one end of the drive shaft that couples with the paddle coupler of the undulation paddle. Rotation of the motor rotor imparts a precessional motion to the undulation paddle by means of the undulation coupler.

A primary object of the present invention is to provide an integrated heart-lung machine that utilizes an undulation pump, provides blood oxygenation and optimally temperature regulation, and is small enough to be placed in close proximity to a sterile patient operating area.

Another object of the invention is to provide a circular undulation pump for use in a heart-lung machine, which undulation pump includes a drive unit with a primary drive shaft and a secondary slanting shaft connected to a precession body, which precession body translates precessional motion to drive the circular undulation pump.

A primary advantage of the present invention is that it provides an integrated heart-lung machine with a low circuit priming volume for use in patient surgery, especially open-heart surgery.

Another advantage of the present invention is that it improves recovery of the patient, provides a reduction in the amount of drugs necessary following surgery, and reduces the amount of blood transfusion that is required as a result of surgery.

Yet another advantage of the present invention is a reduction in medical expenses related to heart surgery.

The present invention also improves the efficiency of space utilization in operating rooms and allows the practice of open heart surgery in small operating rooms.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
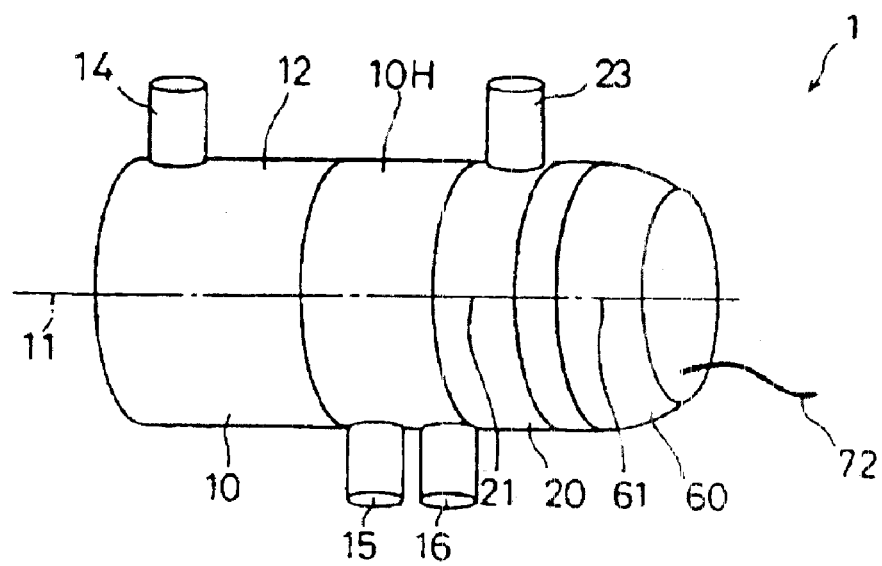
FIG. 1 illustrates the artificial heart-lung apparatus of the present invention.

The present invention relates to an apparatus and methods for performing extracorporeal blood oxygenation and circulation. The invention also relates to a small integrated apparatus which provides membrane oxygenation with minimum priming volume and, by reason of its compact size, can be placed in close proximity to a sterile patient operating area. The artificial heart-lung apparatus of the present invention includes a single unit in which a cylindrical artificial lung with a heat exchanger is connected in series to an undulation pump and a removable drive unit. Within the artificial heart-lung apparatus the cylindrical artificial lung, or oxygenator, includes gas permeable membranes for the purpose of gas exchange. The heat exchanger performs cooling or heating of the blood inside the artificial lung. The cylindrical undulation pump supplies blood to the artificial lung and returns blood to the patient. A pump drive unit is attached to the cylindrical undulation pump.

In a preferred embodiment, the central axes of the oxygenator and the undulation pump are coaxial, and more preferably, the central axes of the oxygenator, the undulation pump and the drive unit are all coaxial. The drive unit is preferably cylindrical in shape, and is further preferably detachable from the pump. The heat exchanger may be an integrated part of the oxygenator, and preferably positioned so as to allow circulating blood and heating or cooling media to run alternately alongside one another.

The artificial heart-lung apparatus of the present invention is thus generally comprised of a cylindrical oxygenator having an inlet port at one end, a cylindrical blood pump having an outlet port that is connected to an inlet port of the oxygenator, and a detachable drive unit which drives the pump. The artificial lung and the blood pump can be constructed as one unit. The drive unit is positioned on the opposite side of the blood pump from the oxygenator, and is optionally detachable.

The blood pump is generally cylindrical in shape with a generally toroidal pump chamber, which pump chamber has a generally fan-shaped or bilaterally symmetrical trapezoidal-shaped cross section, such that the width of the chamber increases gradually from the center to the outermost interior chamber wall. The pump chamber has a flexible inner wall which provides a liquid-tight circumferential seal. A circular, washer-shaped undulation paddle, which transits the flexible inner wall on or near the inner ring of the undulation paddle, pumps by a precessional motion blood received in an inlet port out an outlet port. Thus the undulation paddle moves in a precessional or undulation motion, but does not itself rotate. The undulation paddle is attached, preferably removably attached, at its center portion and on the non-blood side of the flexible inner wall, to a coupler providing precessional motive force.

The drive unit has a motor rotor, a drive shaft that is angled with respect to a motor rotor shaft, and a coupler located at the end of the angled drive shaft, which coupler is in communication with the center portion of the undulation paddle. The coupler thus has a precessional movement, and is driven by the continual rotation of the motor rotor. The coupler precessional movement drives the undulation paddle, also in a precessional motion.

The artificial lung includes a heat exchanger that contains a medium capable of exchanging heat with blood and is located along the axis of the artificial lung. The artificial lung also has a gas exchanger which supplies oxygen to the blood, removes carbon dioxide, and is preferably located alongside of the inner wall of the casing.

The artificial lung can be used as part of an emergency life support system in a patient with decreased lung function. The decreased lung function may be the result of drowning, pneumonia, or any other disease or disorder that results in abnormally low lung function. Blood is removed from the patient's body through blood draw cannula 5 inserted into the vena cava. The blood completes an extracorporeal circuit in which it absorbs oxygen, diffuses carbon dioxide, and returns to the patient's body through blood return cannula 6 which is also inserted into the vena cava. Blood may optionally be heated or cooled before it is returned to the patient's body.

Figure 2:
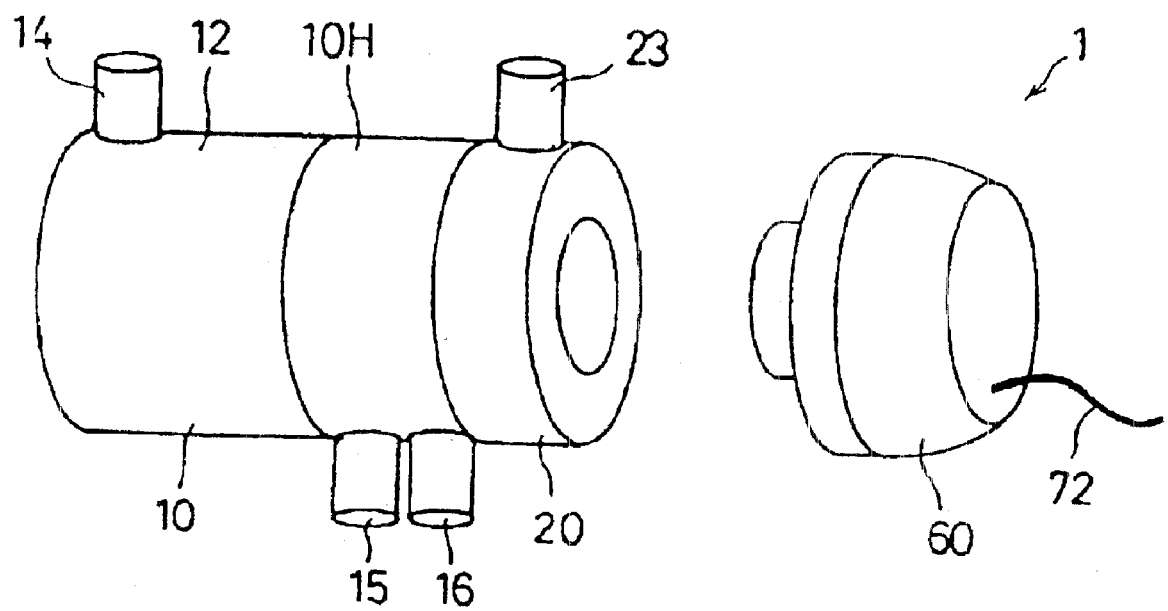
FIG. 2 illustrates the artificial heart-lung apparatus with the drive unit separated from the undulation pump.

In FIGS. 1 and 2 the apparatus of the present invention is generally designated at 1. The apparatus consists of cylindrical oxygenator 10, cylindrical undulation pump 20 to supply blood to oxygenator 10, and cylindrical drive unit 60 to drive undulation pump 20. Oxygenator 10 contains as a part of its cylindrical body cylindrical heat exchanger 10H for heating or cooling blood that passes through oxygenator 10. Oxygenator 10 contains a plurality of semi-permeable, hollow fibers in a mat, bundle, or other array that form a filter. A gas, preferably oxygen, is diffused through the hollow fibers of the filter. As blood passes through the filter it absorbs oxygen from the hollow filter fibers and diffuses carbon dioxide into the hollow filter fibers in an equilibrium reaction.

Oxygenator 10, undulation pump 20, heat exchanger 10H and drive unit 60 are all cylindrical. In this context, cylindrical means in a shape or form in which cross sections of the parts are continuous in the direction of the axes of the cross section, such that the axes lines are superimposable or coaxial, such as along common axis 11, 21 and 61. The components of the present invention are preferably placed in series in the following order: oxygenator 10, heat exchanger 10H, undulation pump 20, and drive unit 60. It is possible and contemplated to place the components in a different order. For example, the components can be placed in order of heat exchanger 10H, oxygenator 10, undulation pump 20, and drive unit 60.

An artificial heart-lung apparatus thus constructed and placed in close proximity to the surgical area is utilized to perform substitute functions of a patient's heart and lungs during surgery where the heart has been stopped. It does this by removing blood from the patient through tubing (not shown) that leads to artificial heart-lung apparatus 1, heating or cooling the blood, supplying oxygen and simultaneously removing carbon dioxide from the blood (a process known as gas exchange), and returning the blood to the patient through tubing (not shown).

Heat Exchanger

The cylindrical heat exchanger 10H contains channels to move blood from undulation pump 20 to oxygenator 10. Channels of media that can be set to a desired temperature are placed side by side with the blood channels. This arrangement allows temperature regulation of the blood by heat exchange between the blood and media. Water, air, and other kinds of gases can be used as media. Media enter into the heat exchanger through media inlet port 15, located on the outer surface of the heat exchanger 10H, and exit through media outlet port 16.

Oxygenator

The cylindrical oxygenator 10 is attached to the heat exchanger 10H. The oxygenator has blood channels of multi-porous cylindrical material (not shown) with hollow fiber membranes disposed on the outer surface of the blood channel, thereby serving as a gas exchanger for blood gas exchange. The oxygenator's multi-porous cylindrical blood channel is connected to the blood channel of the heat exchanger 10H (not shown). Blood enters from the heat exchanger blood channel, exchanges gas at the hollow fiber membrane, and then exits from the outlet located on the surface of casing 12. The oxygen inlet and outlet ports are not shown in the drawing due to their small size. An apparatus composed of a heat exchanger and an oxygenator as one unit are well known in the art. U.S. Pat. No. 5,230,862 discloses gas permeable fibers or tubes, and arrangements thereof, which may be employed in this invention, and is incorporated herein by reference.

Undulation Pump

Figure 3A:
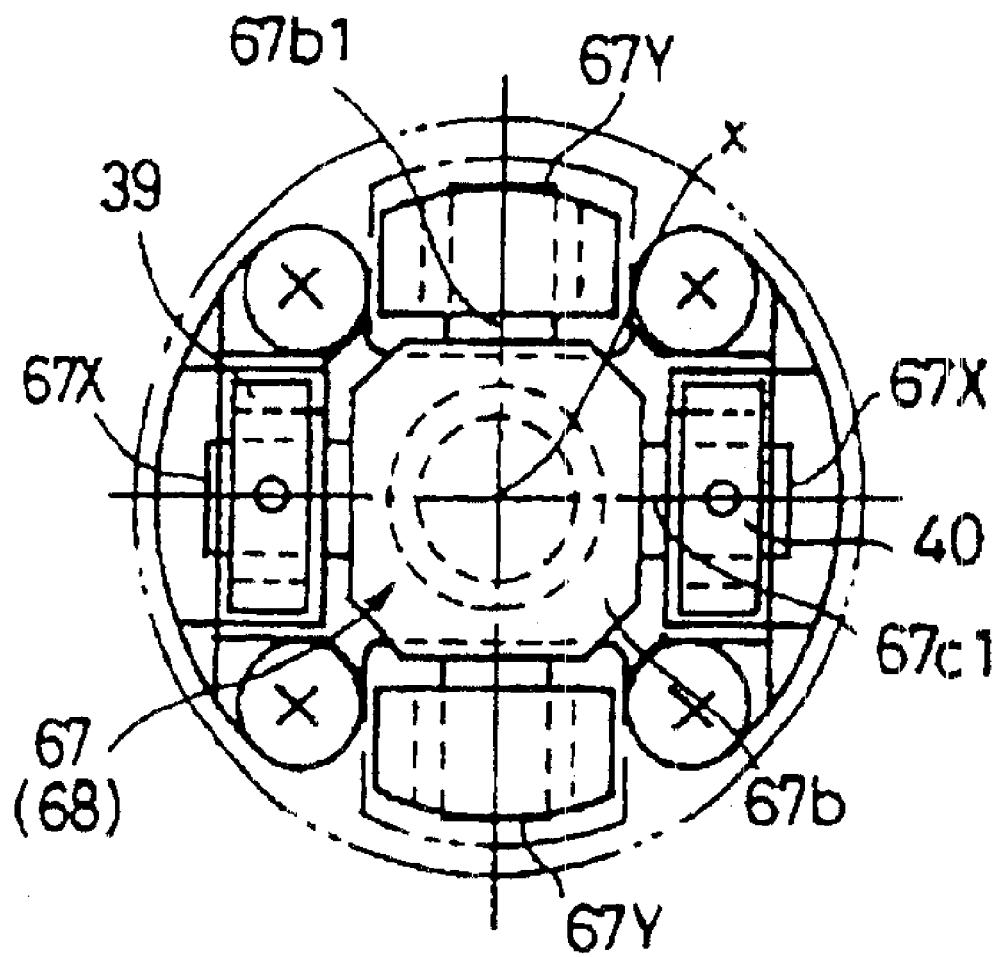
FIG. 3A is a two-dimensional top view drawing of the cross bearing body.
Figure 3B:
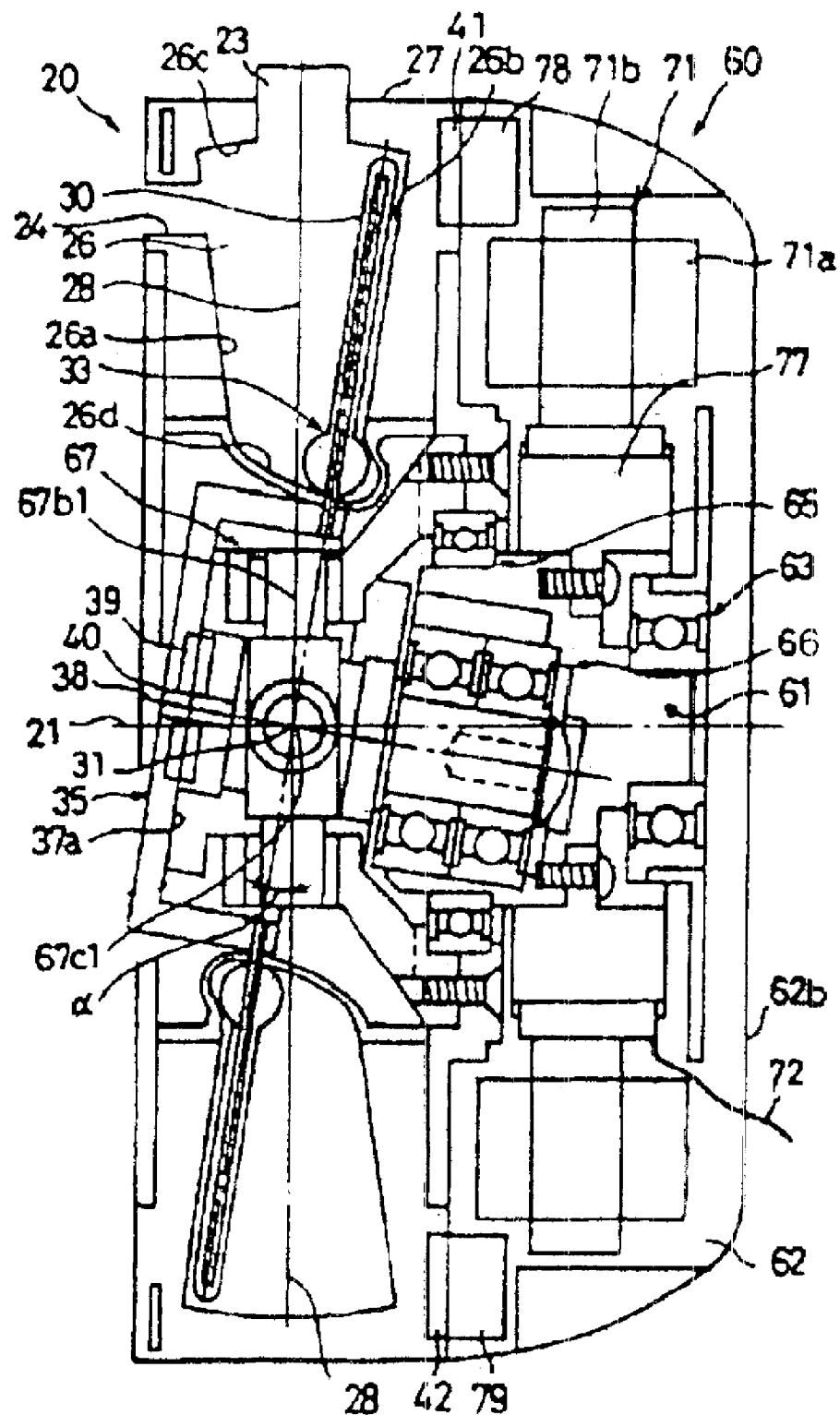
FIG. 3B is a vertical cross section of the drive unit and the undulation pump.
Figure 4A:
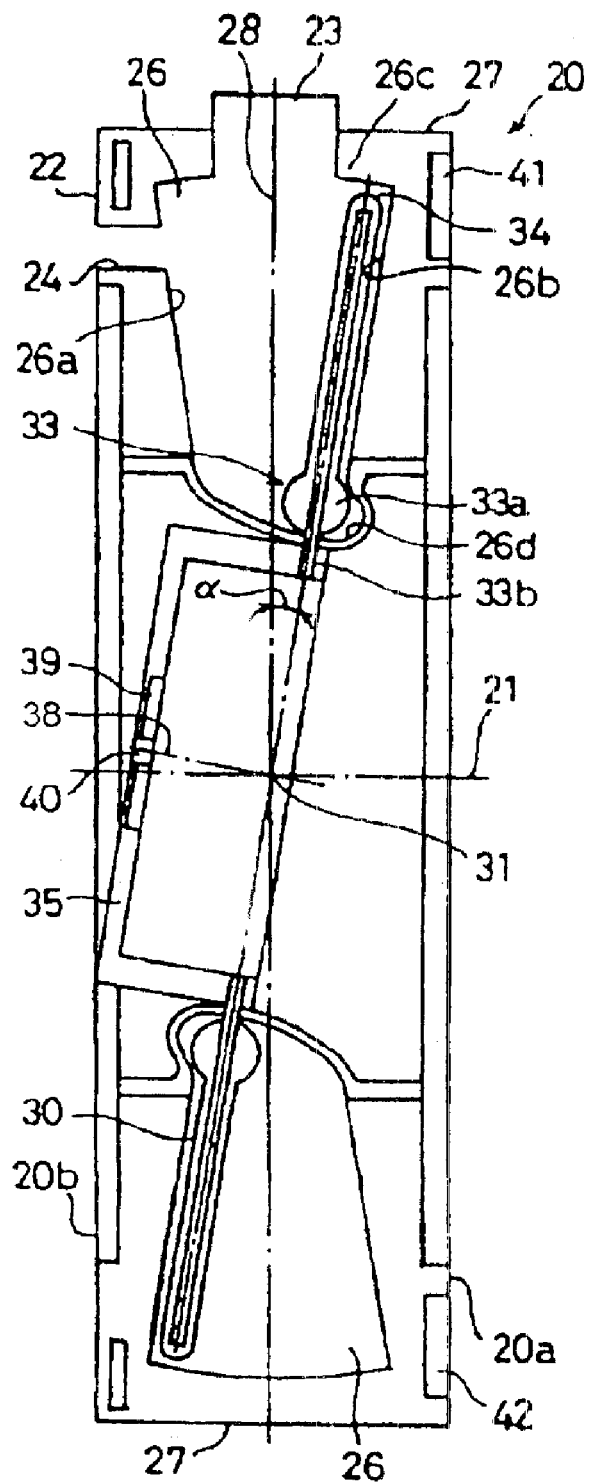
FIG. 4A is a vertical cross-section of the undulation pump including the toroidal-shaped pump chamber.

Undulation pump 20, as shown in FIGS. 3B and 4A, has blood inlet port 23 on the outer surface of the cylindrical casing with center axis 21. The cross section surface 20b of cylindrical casing 20 faces heat exchanger 10H and has blood outlet port 24 that is connected to the blood channel of heat exchanger 10H. Inlet port 23 and outlet port 24 are connected to cylindrical pump chamber 26. Blood coming into the pump chamber from inlet port 23 can be driven out, through pump chamber 26, to the heat exchanger via outlet port 24. Outlet port 24 is directly connected to the blood port (not shown) of the oxygenator, such as heat exchanger 10H, at the pump side facing the undulation pump. Preferably outlet port 30 is directly connected to the next component in series, such as heat exchanger 10H, by means of a direct connection not employing tubing, either flexible or solid. Direct serial connection of the oxygenator and the pump permits the length of the tubing by which blood is transported to be considerably reduced or even eliminated, thus resulting in a substantial reduction of the blood priming volume of the system.

Figure 4B:
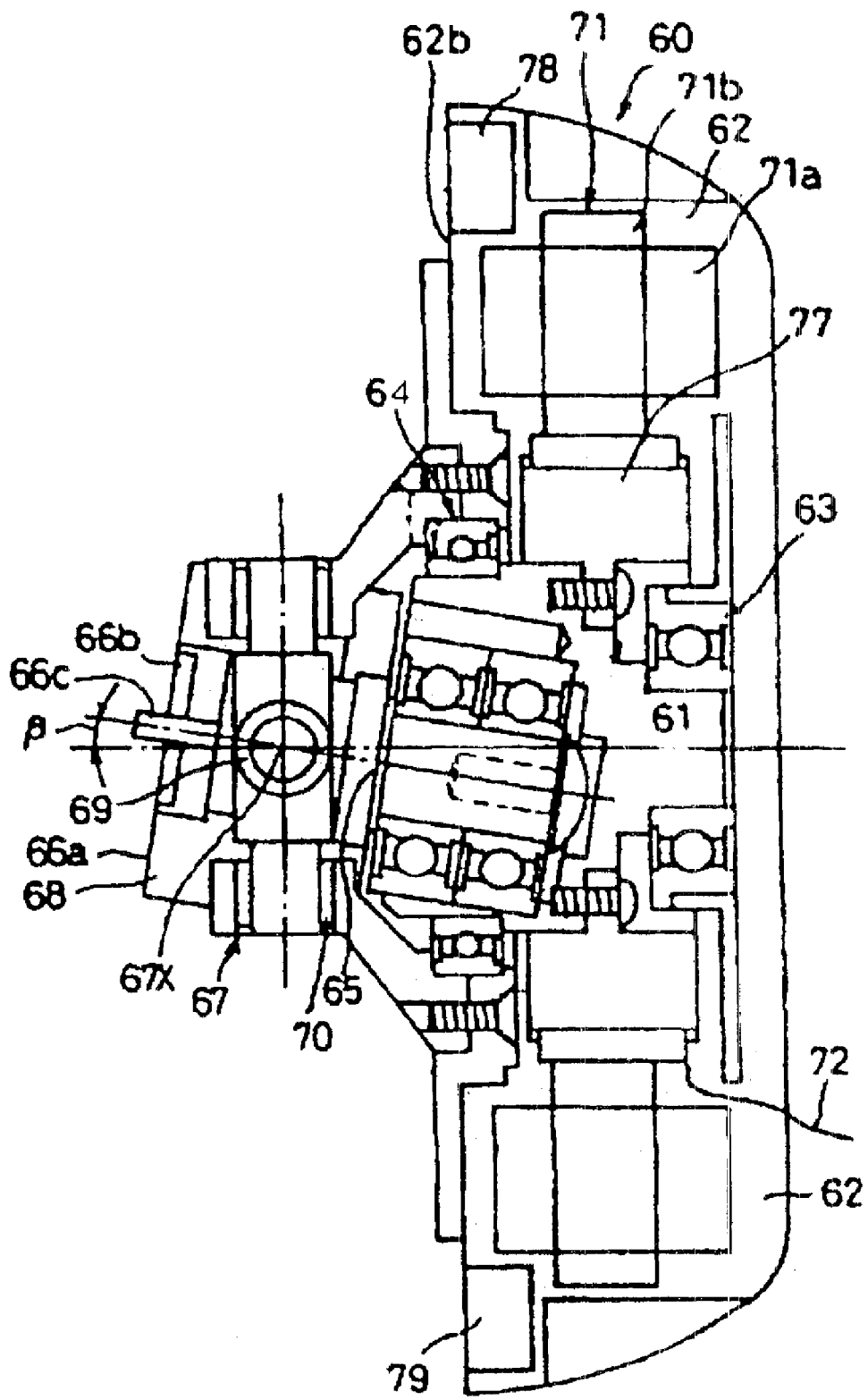
FIG. 4B is a vertical cross-section of the drive unit.
Figure 4C:
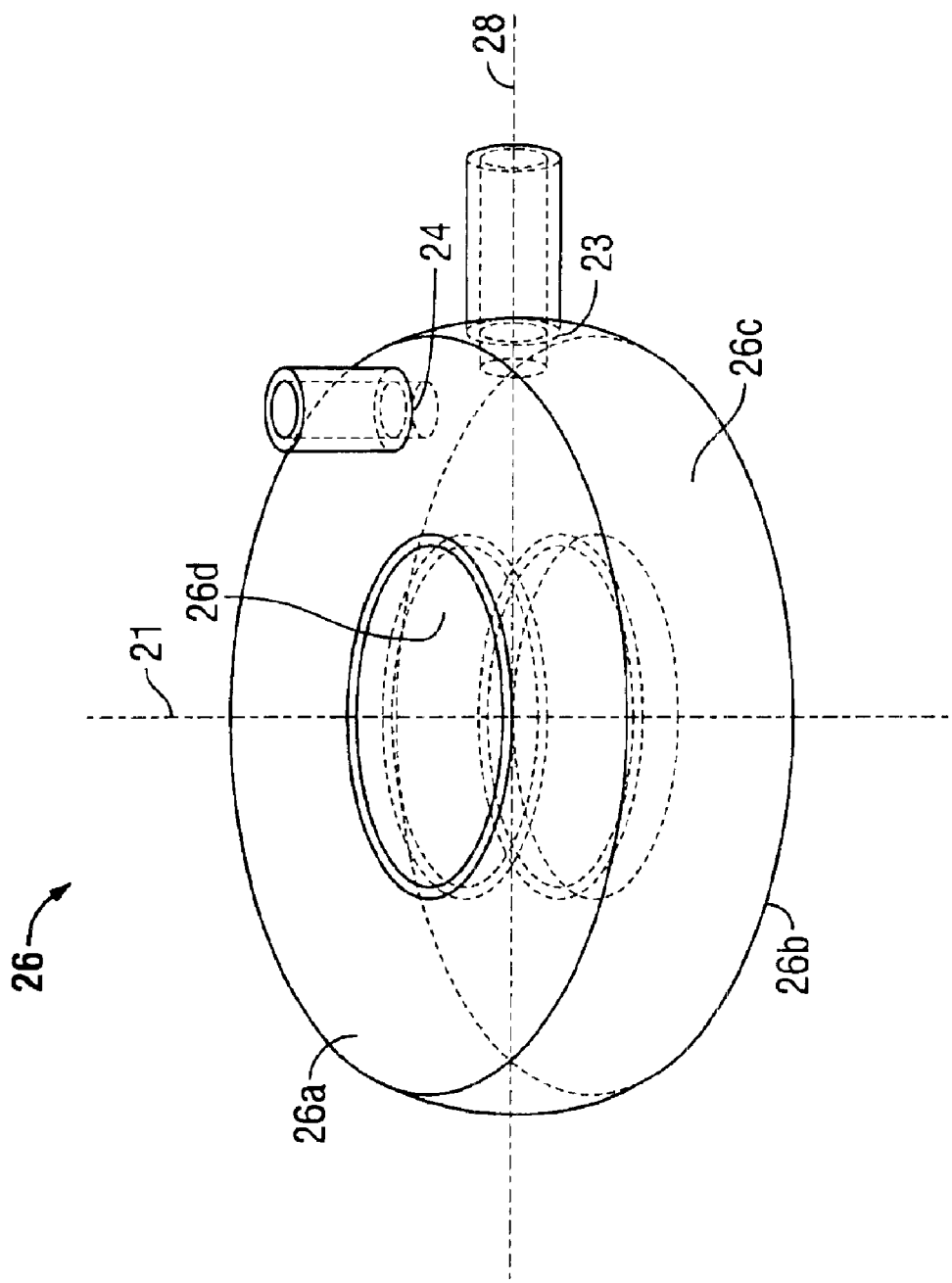
FIG. 4C depicts the three-dimensional structure of the toroidal-shaped pump chamber of the undulation pump.

As shown in FIGS. 3B, 4A and 4C, toroidal-shaped pump chamber 26, viewed from the cross section perpendicular to the axis of cylindrical casing 22, has a fan shape or generally bilaterally symmetrical trapezoidal shape increasing in width from the side of center axis 21 of the cylindrical casing to the outer wall 27. In other words the inner walls of surfaces 20a and 20b, namely 26a and 26b, have a fixed and equal angle α relative to cross section line 28 of casing 22. The toroidal-shaped pump chamber thus is a three-dimensional structure as shown in FIG. 4C that has a circumferential flexible liquid-tight inner wall 26d, two substantially planar angled side walls 26a and 26b, an arc-shaped outer wall 26c, an inlet port 23 and an outlet port 24.

Inner wall 26c is circular and symmetrical to the axis of pump chamber 26, as shown in FIGS. 3B and 4B, describing a circular arc having its center at the point of intersection of center axis 21 of undulation pump 20 and perpendicular cross section 28 of casing 22. Circumferential flexible inner wall 26d, located proximal center axis 21, is a flexible and elastic material.

Undulation paddle 30 has a washer-like shape, and is disposed within the pump chamber 26. Undulation paddle 30 has its center 31 located on center axis 21 of the undulation pump. An interior portion of undulation paddle 30 transits the flexible inner wall 26d of the pump chamber. The outer end 34 of undulation paddle 30 is located close to inner wall 26c of pump chamber 26, but without touching inner wall 26c. The end 33 of undulation paddle 30 located at the side close to its center has end piece 33a with a round cross section and extension 33b projecting inward through the flexible liquid-tight inner wall 26d. In a free condition the direction of the axis of undulation paddle 30 is located on cross section 28 of casing 22.

Extension 33b of undulation paddle 30 is fixed to paddle support 35 which also serves as a coupler. Paddle support 35 has a cup-shaped cross section. The bottom of the cup faces towards heat exchanger 10H. At inner surface 37a of round cup bottom 35, two rectangular magnets are inserted, one on each side, of the center 38 of paddle support 35. There is a hole 40 at the center of each magnet 39. On side surface 20a magnets 41 and 42 are inserted at both ends of casing 22 in the direction of cross section 28 of casing 22.

Inlet port 23, which is connected to pump chamber 26, can be placed at any position on the outer circle of casing 22 or at any position on side surface 20a or 20b. Similarly, outlet port 24, which is connected to pump chamber 26, can be placed at any position on the side surface 20a or 20b or on the outer circle 27 of casing 22.

In an alternative embodiment, a cylindrical pump providing an outlet port of the cylinder end, engageable with an inlet port of an oxygenator, may be employed. While the undulation pump provides certain space and volume advantages, it is to be understood that other pumps, which may similarly be serially arrayed with a drive unit and oxygenator, may be employed in the practice of this invention.

Drive Unit

Drive unit (drive motor unit) 60 drives undulation pump 20 and is removable from the undulation pump as shown in FIGS. 3B and 4B. Drive unit 60 has drive shaft 61, a motor rotor, which is driven together with rotor 77, and further has casing 62 supporting free rotation of drive shaft 61. Casing 62 is bowl-shaped and preferably has a circular bottom. The diameter of the bowl increases gradually towards the circular upper surface.

Drive unit 60 has first bearing 63 and second bearing 64 inside of casing 62 which support the free rotation of drive shaft 61. Third bearing 66 supports slanting shaft 65, which has an inclination of β degree to the center line of drive shaft 61 at cross unit 67. Third bearing 66 thus supports slanted shaft 65 and precession body 68, which precession body 68 comprises a coupler forming the top part of slanted shaft 65. Cross unit 67 has a pair of arms 67X, which coincide with axis X perpendicular to rotation drive shaft 61, and pair of arms 67Y which are perpendicular to axis X (arms 67X). Pair of arms 67X is supported on slanted shaft 65 by bearing 69. Pair of arms 67Y is supported by bearing 70 to allow free rotation, with bearing 70 fixed on casing 62. It is preferable that angle β is the same as angle α or smaller. By means of the bearings provided, the eccentric motion of slanting shaft 65 is translated to precession body 68, such that precession body 68 has a precessional or undulation motion, without precession body 68 itself rotating.

Inside of casing 62 there is stator 71 which drives the rotation of drive shaft 61. There is also electrical wire 72 inside of casing 62 that sends an electrical current to stator 71. Drive shaft 61 rotates when electrical current is sent through wire 72 to stator 71. This results in a precessional motion of precession body 68. Stator 71 consists of coil 71a and stator yoke 71b.

Precession body 68 has a shape that fits inside of paddle support 35. Surface 66a, which faces towards the undulation pump and has a diameter slightly smaller than 37a, has two magnets 66b with polarity opposite to magnets 39. Surface 66a also has two pins 66c that are inserted into hole 40. Magnets 78 and 79 are located on surface 62b of drive unit 60 facing undulation pump unit 20. They are embedded at the positions of magnet 41 and 42 and have opposite polarities, respectively.

Accordingly undulation pump 20 and drive unit 60 are held together by magnets 39 and 66b, magnets 41 and 42, magnets 78 and 79, and are held in a fixed position with two pins 66c inserted into hole 40. Precession body 68 precesses together with paddle support 35.

Thus, undulation paddle 30 can undulate, swaying or undulating as a whole due to precession caused by the motion of body 67b on axes 67b1 and 67c1. The precession of undulation paddle 30 causes undulation inside of pump chamber 26 and results in moving blood from inlet port 23 into chamber 26, and thence to heat exchanger 10H and to oxygenator 10 through outlet port 24.

Heat Exchanger and Oxygenator

Figure 5:
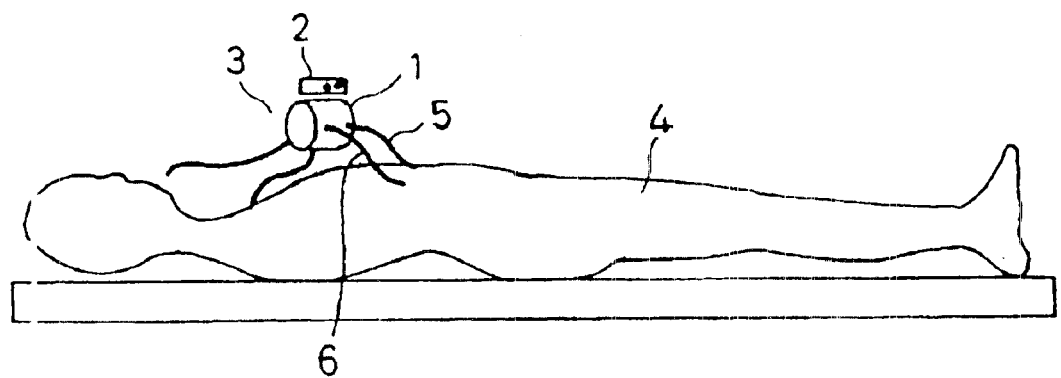
FIG. 5 illustrates the artificial heart-lung apparatus in a surgical operation.

Blood collection cannula 5 from the patient body is connected to inlet port 23 and blood return cannula 6 is connected to output port 14. The blood is drawn into inlet port 23 from blood collection cannula 5 and returned through outlet port 14 after passing through undulation pump 20, heat exchanger 10H, and oxygenator 10, preferably in this order. The blood is returned to the body through blood return cannula 6. Input port 23 and output port 14 can be placed any position within 360 degrees so that the circuit is as short as possible. Undulation pump 20 has a relatively flat or pancake shape. Inlet port 23 and outlet port 24 can be placed in the direction of the axis as well as on the surface of the outer cylinder. Undulation pump 20 provides the same pumping power in normal and reverse rotation. Due to the versatility in shaping and arrangements, the entire apparatus including oxygenator 10, heat exchanger 10H and drive unit 60, can be arranged in series as a single unit. The direct connection between the undulation pump and oxygenator 10 or heat exchanger 10H results in an ultra-small artificial heart-lung apparatus 1 which may be used in operation area 3 of the patient as shown in FIG. 5. Drive unit 60, which has no direct contact with patient blood, is detachable from the undulation pump and therefore can be used repeatedly. As illustrated in FIG. 5, the artificial heart-lung machine is designed to be used in operation area 3 of patient 4 with control unit 2 of apparatus 1.

Figure 6:
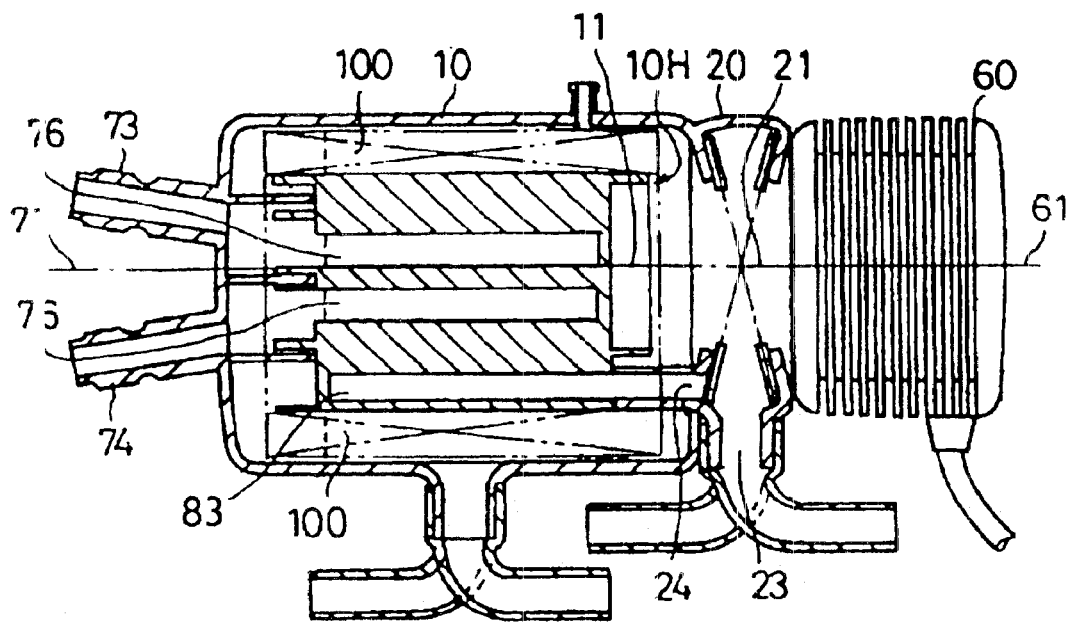
FIG. 6 is a vertical cross section of the artificial heart-lung apparatus.
Figure 7A:
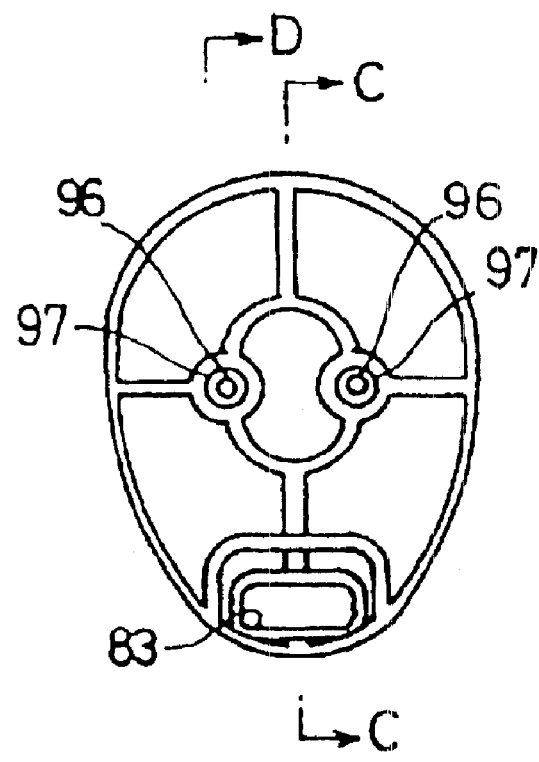
FIG. 7A is a view of the heat exchanger as viewed from the undulation pump side.
Figure 7B:
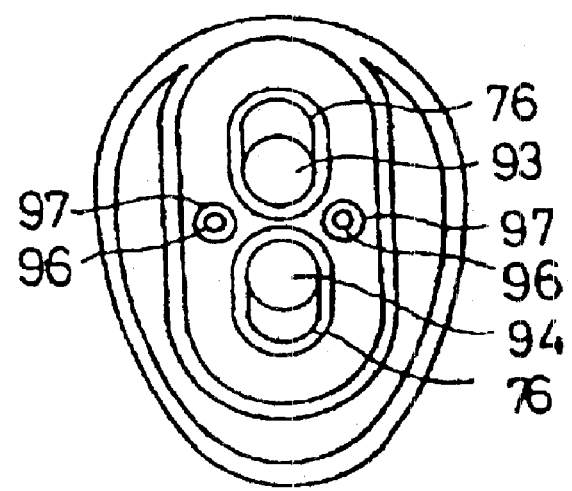
FIG. 7B shows the heat exchanger viewed from the inlet and outlet ports.
Figure 7C:
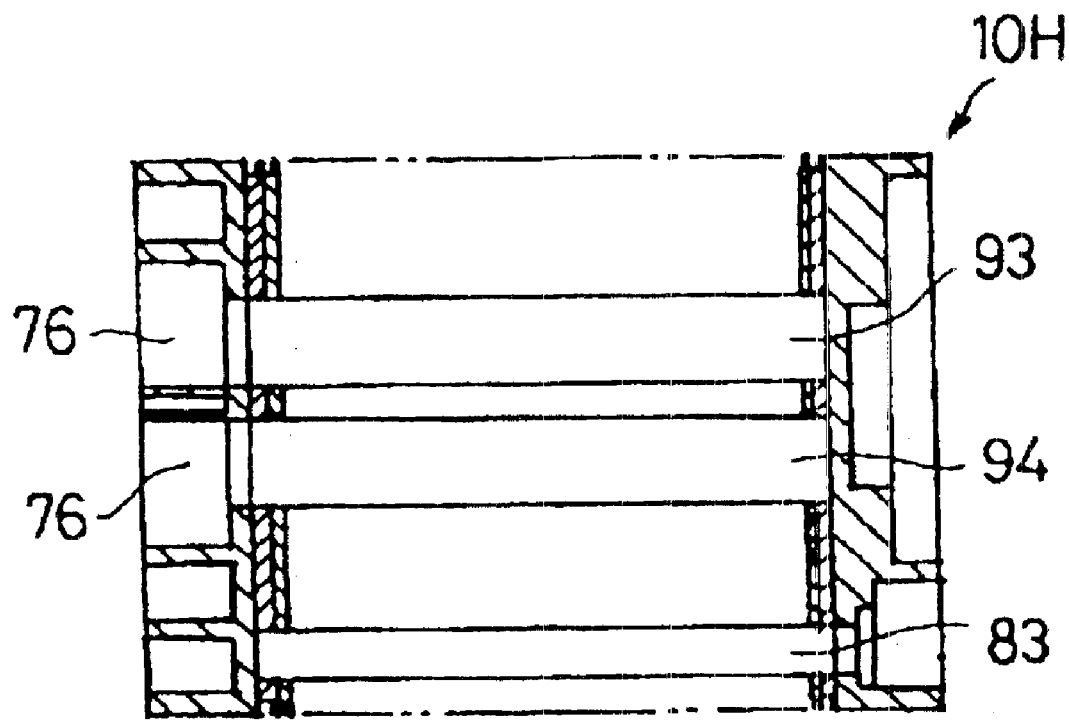
FIG. 7C shows a cross section of the heat exchanger along the plane designated C—C.
Figure 7D:
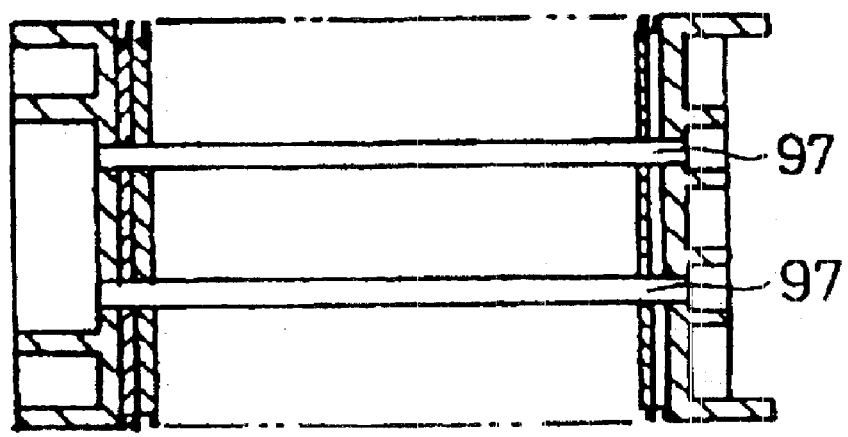
FIG. 7D shows a cross section of the heat exchanger along the plane designated D—D.
Figure 7E:
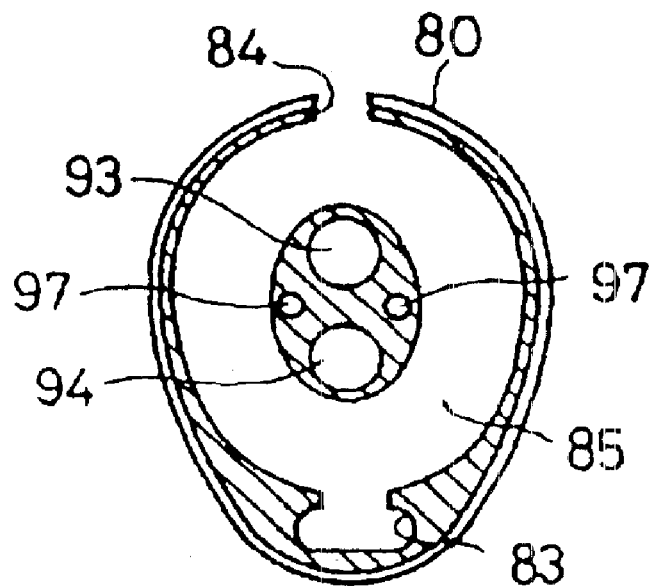
FIG. 7E shows a vertical cross section of the first blood channel plate.
Figure 7F:
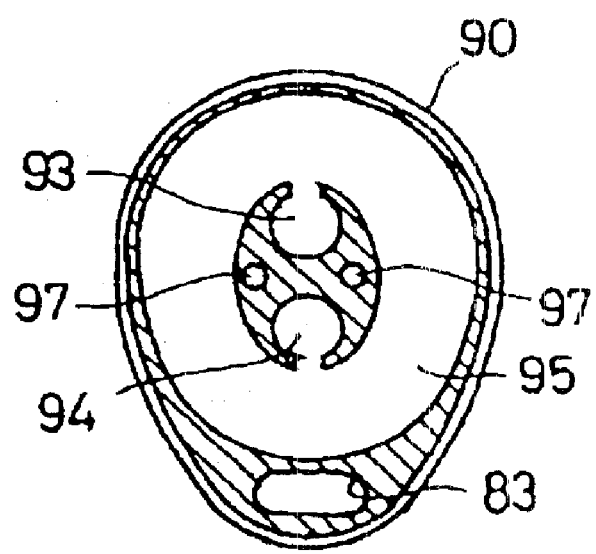
FIG. 7F shows a vertical cross section of the second media channel plate.

The heat exchanger 10H can also be placed inside of oxygenator 10 as shown in FIG. 6. As above, the axes 11, 21, 71 and 61 of cylindrical oxygenator 10, undulation pump 20, heat exchanger 10H and drive unit 60 have the same orientation. The oxygenator 10 and the heat exchanger 10H are constructed as a single unit by surrounding the cylindrical heat exchanger with hollow fiber membrane 100 which serves as a gas exchanger. Cylindrical heat exchanger 10H has an egg-shaped cross section that shows media channel 76, through which appropriate media passes for the purpose of heating or cooling of the blood.

Figure 8:
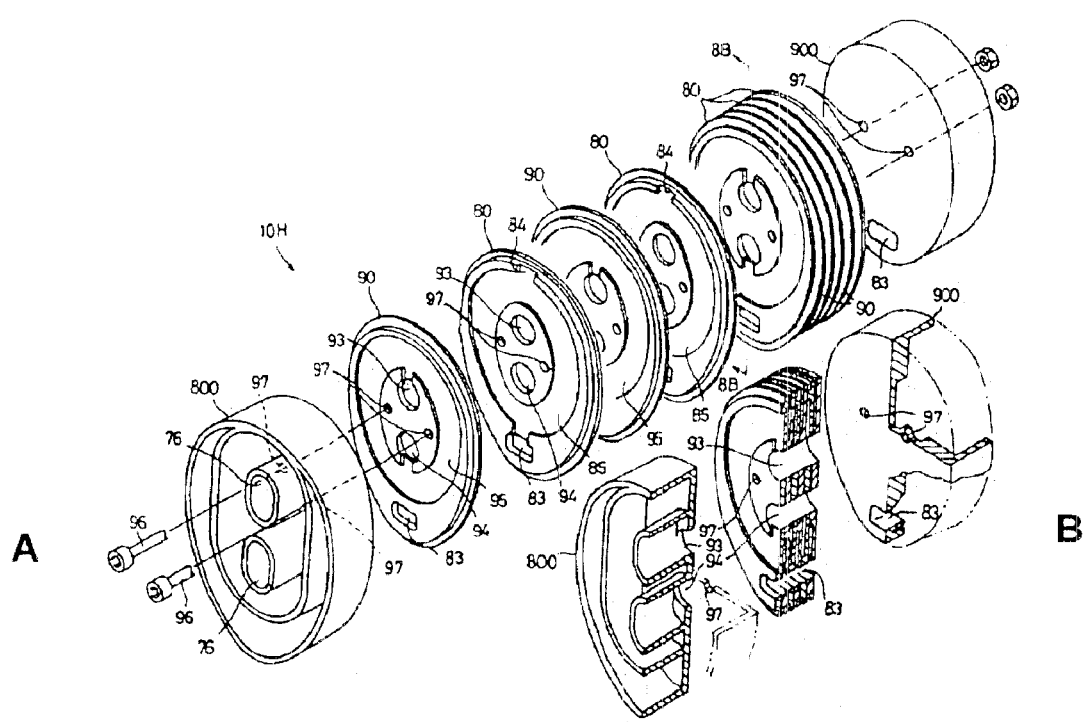
FIG. 8A is an exploded view of the heat exchanger.
FIG. 8B shows a vertical cross section along the plane designated 8B—8B of the heat exchanger.

Heat exchanger 10H, as illustrated in FIGS. 7 and 8, consists of multiple blood channel plates 80 and media channel plates 90. Blood channel plate 80 has a slit connected to blood channel 83 and a slit 84 that opens outward. Media channel plate 90 has 2 slits opening to media channels 93 and 94. First channel plate 80 and second channel plate 90 have the same construction except that the slits are placed alternately in the direction of the axis of oxygenator 10. End plates 800 and 900 are placed at each end to make heat exchanger 10H.

First blood channel plate 80, which is connected to outlet port 24 of the undulation pump, consists of oval channel 83, circular channel 85, and exit channel 84. Oval channel 83 is a hole through which blood is supplied to heat exchanger 10H. Blood from oval channel 83 passes through circular channel 85 and exits through channel (slit) 84 to hollow fiber membrane 100 placed on the outer side of heat exchanger 10H. Two circular channels 93 and 94 inside of the inner circle of circular channel 85 allow media to pass through.

Second media channel plate 90, as shown in FIGS. 7 and 8, is constructed exactly like channel plate 80 with three exceptions: (1) channel (slit) 84 does not exist; (2) there is no slit connecting oval channel 83 and circular channel 95 (equivalent to channel 85 of plate 80); and (3) there are two slits made connecting channel 93 and 94 to circular channel 95. Two circular channels 93 and 94 are connected, one to inlet port 73 and the other to outlet port 74. The two ports 73 and 74 are interchangeable.

Channel plates 80 and 90 can be manufactured from plastics, metals, and or any other appropriate materials by any method including moldings, etchings, or any other method employed to make highly precise channels. Channel plates 80 and 90 are held together using two bolts 96 which go through holes 97 between the two end plates 800 and 900. End plate 800 is equipped with openings around media channel 76 that are connected to inlet port 73 and outlet port 74, circular channels 93 and 94, and holes 97. End plate 900 is positioned on the undulation pump side and has oval channel 83 and hole 97 at the positions each corresponding to their positions of first channel plate 80 and second channel plate 90. Blood running through first channel plate 80 can be effectively cooled or heated by the media running through adjacent second channel plate 90 because circular channel 85 of first channel plate 80 and circular channel 95 of the second channel plate 90 are placed side by side in the direction of axis 71 of heat exchanger 10H.

The path of blood through the artificial heart-lung machine is as follows. Blood is removed from the patient through a blood draw cannula 5 that leads to the artificial heart-lung apparatus 1. Blood enters undulation pump 20 through blood inlet port 23 and arrives in cylindrical pump chamber 26. Blood is pumped out of pump chamber 26 through outlet port 24 by the rapid precession motion of undulation paddle 30.

Blood leaves outlet port 24 of undulation pump 30 and enters heat exchanger 10H through oval channel 83. Blood passes through circular channel 85 of blood channel plate 80 where its temperature is regulated by heat exchange with media in adjacent circular channel 95 of media channel plate 90. The media enter the heat exchanger 10H through inlet port 15 and exit through outlet port 16. Blood passes through circular channel 85 and exits the heat exchanger 10H via channel 84 to cylindrical oxygenator 10.

Blood enters oxygenator 10 and passes among hollow fibers 100 for gas exchange. Oxygen diffuses out from the inner lumen of the hollow fibers 100. As oxygen-deficient blood passes adjacent to the fibers it absorbs oxygen and releases carbon dioxide in an equilibrium reaction. Carbon dioxide from the blood, diffused into the inner lumen of the hollow fibers 100, and residual oxygen exit through gas outlet port (not shown) into the air. Blood exits oxygenator 10 through outlet port 14 located on the surface of casing 12. Blood is returned to the patient via blood return cannula 6 and thus completes its extracorporeal circulation.

The invention further includes a method of providing extracorporeal blood circulation and oxygenation, with concurrent removal of carbon dioxide, by means of the heart-lung apparatus as described.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An integrated artificial heart-lung apparatus, comprising:
   an undulation pump with a precessional undulation paddle;
   an oxygenator;
   a heat exchanger; and
   a removable drive unit that is attached to the undulation pump, wherein the undulation pump, oxygenator and heat exchanger are interconnected in series.

2. The heart-lung apparatus of claim 1, wherein the undulation pump comprises a toroidal-shaped pump chamber with a circumferential flexible liquid-tight inner wall, two substantially angled side walls, an arc-shaped outer wall, an inlet port, an outlet port, and wherein the precessional undulation paddle is circular, transits the flexible liquid-tight inner seal and has a diameter that extends to the arc-shaped outer wall of the pump chamber.

3. The heart-lung apparatus of claim 2, wherein the undulation pump further comprises a paddle coupler centrally disposed on the undulation paddle, and not within the pump chamber, the paddle coupler in communication with a precessional coupler forming a part of the drive unit.

4. The heart-lung apparatus of claim 1, wherein the undulation pump, oxygenator and drive unit are all coaxially disposed within a cylindrical casing.

5. The heart-lung apparatus of claim 1, wherein the undulation pump comprises an outlet port in direct communication with an inlet port of the oxygenator.

6. An artificial heart-lung apparatus, comprising:
   a cylindrical oxygenator with hollow fiber membranes for blood gas exchange; and
   a cylindrical undulation pump with a circular precessional undulation paddle, coaxial with the oxygenator, to pump blood to the oxygenator.

7. The heart-lung apparatus of claim 6, further comprising a cylindrical drive unit to drive the undulation pump.

8. The heart-lung apparatus of claim 7, wherein the oxygenator, the undulation pump, and the drive unit are all coaxial.

9. The heart-lung apparatus of claim 7, wherein the drive unit is removable from the undulation pump.

10. The heart-lung apparatus of claim 6, further comprising a heat exchanger with at least one first channel plate that forms a blood channel and a second channel plate that forms a media channel for heating or cooling of blood.

11. The heart-lung apparatus of claim 10, wherein the heat exchanger comprises a plurality of first channel plates that provide blood running channels and a plurality of second channel plates that provide media running channels, disposed such that the first and second channel plates are adjacent to and alternating with each other.

12. The heart-lung apparatus of claim 6, further comprising a heat exchanger located inside of the oxygenator.

13. An artificial heart-lung apparatus comprising:
   a cylindrical blood pump with a circular precessional undulation paddle and an outlet port at one end that is directly connectable to an inlet port of an oxygenator; and
   a drive unit that is removable from the blood pump.

14. The heart-lung apparatus of claim 13, further comprising a cylindrical oxygenator directly connected to the blood pump.

15. The heart-lung apparatus of claim 14, further comprising a heat exchanger for heat exchange between blood and media as they pass along a center part of the axis of the heart-lung apparatus.

16. The heart-lung apparatus of claim 15, wherein the heat exchanger comprises a first channel plate that forms a blood channel and a second channel plate that forms a media channel for cooling or heating blood, the first channel plate and second channel plate placed alternately side by side in the direction of the axis of the heat exchanger.

17. The heart-lung apparatus of claim 13, wherein the blood pump comprises:
   a toroidal-shaped pump chamber with a circumferential flexible liquid-tight inner wall, two substantially angled side walls, an arc-shaped outer wall, an inlet port and an outlet port;
   a circular undulation paddle that transits the flexible liquid-tight inner wall and has a diameter that extends to the arc-shaped outer wall of the pump chamber; and a paddle coupler for receiving a precessional motion from the drive unit centrally disposed on the undulation paddle and not within the pump chamber.

18. The heart-lung apparatus of claim 17, wherein the drive unit comprises:

a motor rotor and a free rotating drive shaft angled with respect to the axis of the motor rotor;

a drive shaft coupler at one end of the drive shaft that couples with the paddle coupler of the undulation paddle; whereby rotation of the motor rotor imparts a precessional motion to the drive shaft coupler which in turn imparts a precessional motion to the undulation paddle by means of the undulation coupler.

19. The heart-lung apparatus of claim 13, wherein the drive unit is connected opposite from the side of the oxygenator.

* * * * *